(12) United States Patent
Kailas et al.

(10) Patent No.: US 8,527,213 B2
(45) Date of Patent: Sep. 3, 2013

(54) MONITORING WELLNESS USING A WIRELESS HANDHELD DEVICE

(75) Inventors: Aravind Kailas, Atlanta, GA (US); Chia-Chin Chong, Santa Clara, CA (US); Fujio Watanabe, Union City, CA (US)

(73) Assignee: NTT DoCoMo, Inc., Tokyo (JP)

( * ) Notice: Subject to any disclaimer, the term of this patent is extended or adjusted under 35 U.S.C. 154(b) by 458 days.

(21) Appl. No.: 12/827,963

(22) Filed: Jun. 30, 2010

(65) Prior Publication Data

US 2011/0022332 A1 Jan. 27, 2011

Related U.S. Application Data

(60) Provisional application No. 61/227,388, filed on Jul. 21, 2009, provisional application No. 61/233,365, filed on Aug. 12, 2009.

(51) Int. Cl.
*G01N 31/00* (2006.01)
*G01N 33/48* (2006.01)
*G01N 33/50* (2006.01)

(52) U.S. Cl.
USPC .............................. 702/32; 702/19

(58) Field of Classification Search
USPC .............................. 702/42, 19, 32
See application file for complete search history.

(56) References Cited

U.S. PATENT DOCUMENTS

| | | | |
|---|---|---|---|
| 2003/0135097 A1* | 7/2003 | Wiederhold et al. | 600/301 |
| 2004/0087839 A1* | 5/2004 | Raymond et al. | 600/300 |
| 2004/0176991 A1* | 9/2004 | McKennan et al. | 705/10 |
| 2005/0236004 A1* | 10/2005 | Magnuson et al. | 128/898 |
| 2006/0047187 A1* | 3/2006 | Goyal et al. | 600/300 |
| 2006/0205564 A1 | 9/2006 | Pererson | |
| 2009/0234666 A1* | 9/2009 | Crawford et al. | 705/1 |
| 2010/0204616 A1* | 8/2010 | Shears et al. | 600/595 |
| 2010/0274102 A1* | 10/2010 | Teixeira | 600/301 |

OTHER PUBLICATIONS

Dictionay.com for term "monitor".*
PCT Search Report and Written Opinion (PCT/US10/41999) dated Sep. 17, 2010.
W. Liao et al. "A Real-Time Human Stress Monitoring System Using Dynamic Bayesian Network," Proceedings of the 2005 IEEE Computer Society Conference on Computer Vision and Pattern Recognition, 2005, 8 pages.
M. S. Sharawi, et al. "Design and Implementation of a Human Stress Detection System: A Biomechanics Approach," Proceedings of the 5th International Symposium on Mechatronics and its Applications, Amman, Jordan, May 27-29, 2008.

(Continued)

*Primary Examiner* — Michael Nghiem
(74) *Attorney, Agent, or Firm* — Haynes and Boone, LLP

(57) ABSTRACT

A method for detecting a subject's stress level associated with an activity includes (a) connecting the subject to a sensor that senses a value of a biometric; (b) during the activity, (i) repeatedly sensing the value of the biometric over each of a plurality of time windows; and (ii) computing, for each time window, a deviation in the sensed values of the biometric; and (c) detecting the stress level based on the computed deviations. In one implementation, the value of the biometric is a skin temperature measurement. The method may be implemented as an application in a wireless handheld device, such as a cellular telephone.

8 Claims, 10 Drawing Sheets

(56) References Cited

OTHER PUBLICATIONS

K. McLellan et al. "The effects of skin moisture and subcutaneous fat thickness on the ability of the skin to dissipate heat in young and old subjects, with and without diabetes, at three environmental room temperatures," Medical Engineering & Physics 31 (2009) 165-172.

H. Ho et al. "Contribution of thermal cues to material discrimination and localization," Perception & Psychophysics 2006, 68(1), 118-128.

E. Cope "Estimating Human Movement Using a Three Axis Accelerometer," Mar. 9, 2009, 79 pages.

M. Raya et al. "Adaptive Noise Cancelling of Motion Artifact in Stress ECG Signals Using Accelerometer," Proceedings of the Secong Joint EMBX/BMES Conference, Oct. 23-26, 2002, pp. 1756-1757.

T. R. Burchfield et al. "Accelerometer-Based Human Abnormal Movement Detection in Wireless Sensor Networks," International Conference on Mobile Systems, Applications and Services, 2007.

M. Schultz et al. "The Biofeedback Stress Test," Developments in Business Simulation and Experiential Learning, vol. 29, 2002.

A. Mannini et al. "Machine Learning Methods for Classifying Human Physical Activity from On-Body Accelerometers," Sensors 2010, 10, 1154-1175, 2010.

H. Yamana, "Embedded System for Monitoring Human Activities Using 3-Axis Accelerometer" University of Texas at Arlington, Dec. 2007, 84 pages.

M. Sung et al. "Shiver Motion and Core Body Temperature Classification for Wearable Soldier Health Monitoring Systems" Proceedings of the Eighth International Symposium of Wearable Computers, 2004.

M. Wailoo et al. "Home Monitoring of Body Temperature Patterns in Infancy" IEE Colloquium on Data Logging of Physiological Signals, Nov. 23, 1995.

H. Ho et al. "Material identification using real and simulated thermal cues," Conf Proc IEEE Eng Med Biol Soc. 2004;4:2462-5.

H. Asada et al. "Towards the development of wearable blood pressure sensors: a photo-plethysmograph approach using conducting polymer actuators," Conf Proc IEEE Eng Med Biol Soc. 2005;4:4156-9.

S. Park et al. "Wearable Sensor Systems: Opportunities and Challenges," Proceedings of the 2005 IEEE Engineering in Medicine and Biology 27th Annual Converence, Sep. 1-4, 2005.

X. Yang et al, "Advances in Hyperthermia Technology," Proceedings of the 2005 IEEE Engineering in Medicine and Biology 27th Annual Converence, Sep. 1-4, 2005.

F. Vallais et al. "Comparison of BRS Estimates during Mild Dynamical Exercise and Recovery," Proceedings of the 29th Annual International Conference of the IEEE EMBS, Aug. 23-26, 2007.

S. Park et al. "Development of Bio-Signal Measurement System for Sports Healthcare," 30th Annual International IEEE EMBS Conference, Aug. 20-24, 2008.

J. Bloemsaat et al, "Differential Effects of Mental Loasd on Proximal and Distal Arm Muscle Activity" Exp. Brain Res, 2005.

H. Ho et al, "Thermal Model for Hand-Object Interactions" Symposium on Haptic Interfaces for Virtual Environment and Teleoperator Systesm, 2006.

T. Higuchi et al. "Freezing degrees of freedom under stress: Kinematic evidence of constrained movement strategies" Human Movement Science 21, pp. 831-846, 2002.

M. Hanlon et al. "Real-Time Gait Event Detection Using Wearable Sensors" Gait & Posture 30 (2009) 523-527.

W. Liao, et al. "A Decision-Theoretic Model for Stress Recognition and User Assistance," Proc. AAAI, pp. 539-534, 2005.

E. Ehrlenspiel "Dissertation: Choking Under Pressure—Attention and Motor Control in Performance Situations," Oct. 2006.

H. Ho et al. "Development and Evaluation of a Thermal Display for Material Identification and Discrimiation," ACM Transacations on Applied Perception, vol. 4, No. 2, Article 13, Jul. 2007.

K. Song et al. "Multi-Person Pose Recognition Using a Zigbee Sensor Network," Proceedings of the 17th World Congress the International Federation of automatic Control, Jul. 6-11, 2008.

S. Yoon et al. "Adaptive Motion Artifacts Reduction Using 3-Axis Accelerometer in E-Textile ECG Measurement System," J Med Syst (2008) 32: 101-106.

"Taking Body Temperature, Inside Out" Jan. 2006, IEEE Spectrum, pp. 13-15.

Y. Chen et al. "Design Clinic Patient Body Temperature Wireless Remote Concentration Monitor System Based on VI" 2009 First International Workshop on Education Technology and Computer Science, 2009 IEEE.

A. Lymberis "Wearable Health Systems and Applications: The Contribution of Information & Communication Technologies" Proceedings of the 2005 IEEE Engineering in Medicine and Biology 27th Annual Conference, Sep. 1-4, 2005.

J. F. O'Brien, T. E. Bernard, and W. L. Kenney, "Personal Monitor to Protect Workers from Heat Stress," Proc. Conf. Human Factors and Power Plants, 1988.

D. G. Park, S. C. Shin, S. W. Kang, and Y. T. Kim, "Development of Flexible Self Adhesive Patch for Professional Heat Stress Monitoring Service," Proc. $27^{th}$ Annual Int. IEEE EMBS Conf., Sep. 2005.

I. Pavlidis et al. "Continuous Physiological Monitoring," Proceedings of the 25th Annual International Conference of the IEEE EMBS, Sep. 17-21, 2003.

E. Toba et al. "Non-Invasive Measurement System for Human Respiratory Condition and Body Temperature" Proceedings of the 1994 IEEE International Conference on Multisensor Fusion and Integration for Intelligent Systems, Oct. 2-5, 1994.

C. Wong et al. "Development of a Portable Multi-Functional Patient Monitor" Proceeings of the 22nd Annual EMBS International Conference, Jul. 23-28, 2000.

W. Van Marken Lichtenbelt et al. "Individual Variation in Body Temperature and Energy Expenditure in Response to Mild Cold" Am J. Physiol Endocrinol Metab 282: Jan. 8, 2002.

J. Chien et al. "A New Wireless-Type Physiological Signal Measuring System Using a PDA and the Bluetooth Technology," IEEE, 2006, 3026-3031.

Z. Mohy-Ud-Din et al. "Wireless Skin Temperature Sensing Patch," IEEE International Conference on Multisensor Fusion and Integration for Intelligent Systems, Aug. 20-22, 2008.

H. Kataoka, H. Yoshida, A. Saijo, M. Yasuda, and M. Osumi, Development of a Skin Temperature Measuring System for Non-Contact Stress Evaluation. Proc. 20th Annual International Conference of the IEEE Engineering in Medicine and Biology Society 2:940-943, 1998.

S. Tanaka et al. "A New Portable Device for Ambulatory Monitoring of Human Posture and Walking Velocity Using Miniature Accelerometers and Gyroscope," 26th Annual International Converence of the IEEE EMBS, Sep. 1-5, 2004.

W. Liao, W. Zhong, Z. Zhu, Q. Ji, and W. Gray, "Toward a Decision-Theoretic Framework for Affect Recognition and User Assistance," International Journal of Human-Computer Studies, 64: 847-873, 2006.

I. G. Finvers, J. W. Haslett, and G. Jullien, "Wireless Temporal Artery Bandage Thermometer," Proc. Biomedical Circuits and Systems Conference, 2006.

Salahuddin, L. et al. "Dependence of Heart Rate Variability on Stress Factors of Stress Response Inventory" IEEE 2007, 4 pages.

Shibli, M. et al. "Modeling and Characterization of a Mechatronics System for Human Stress Detection" 2007 IEEE International Conference on Signal Processing and Communications, Nov. 24-27, 2007, Dubai, United Arab Emirates.

Guenterberg, E. et al. "A Method for Extracting Temporal Parameters Based on Hidden Markov Models in Body Sensor Networks with Inertial Sensors" IEEE Transactions on Information Technology in BioMedicine, 2009.

Zhang, Y. et al. "Active and dynamic information fusion for multisensor systems with dynamic bayesian networks" IEEE Transactions on Systems, Man, and Cybernetics—Part B: Cybernetics, vol. 36, No. 2, Apr. 2006.

Charny, C. et al. "A Whole Body Thermal Mocel of Man During Hyperthermia" IEEE Transactions n Biomedical Engineering, vol. BME-34, No. 5, May 1987.

Bouten, C. et al. "A Triaxial Accelerometer and Portable Data Proessing Unit for the Assessment of Daily Physical Activity" IEEE Transactions on Biomedical Engineering, vol. 44, No. 3, Mar. 1997.

L. A. Jones and H.-N. Ho, "Warm or Cool, Large or Small? The Challenge of Thermal Displays," IEEE Trans. On Haptics, vol. 1, No. 1, pp. 53-70, Jan.-Jun. 2008.

Spence, C. et al. "Tactile and Multisensory Spatial Warning Signals for Drivers" IEEE Transactions on Haptics, vol. 1, No. 2, Jul.-Dec. 2008.

* cited by examiner

MONITORING WELLNESS USING A WIRELESS HANDHELD DEVICE

CROSS REFERENCE TO RELATED APPLICATIONS

The present application is related to and claims priority of (a) U.S. provisional patent application Ser. No. 61/227,388, entitled "Simple Iterative Algorithms to Monitor Wellness using Wireless Handheld Devices," filed Jul. 21, 2009, and (b) U.S. provisional patent application Ser. No. 61/233,365, entitled "Statistical Approach based on Bayesian Models for Monitoring Wellness using Wireless Handheld Devices," filed Aug. 12, 2009. These copending U.S. provisional patent applications are hereby incorporated by reference in their entireties.

BACKGROUND OF THE INVENTION

1. Field of the Invention

The present invention relates to applications of wireless communications. In particular, the present invention relates to applications that can be implemented on a wireless handheld device to monitor wellness of a user of such a device.

2. Discussion of the Related Art

Stress is a key indicator of wellness in humans and is widely regarded as a prime contributor to poor performance and a cause of errors in various human activities. In the online article, entitled "Stress" (the "Panzarino Article"), by P. Panzarino, stress is referred to as a physiological change from homeostasis. The stress response can be thought of as the body's self-defense mechanism that responds to a physiological drift from homeostasis. The typical stress response includes the release of powerful neurotransmitters[1] from the medulla in the adrenal gland. In response to stress, the adrenal medulla secretes two neurotransmitters: epinephrine (also called adrenaline) and norepinephrine (nor-adrenaline). The physiological effects of the fight-or-flight response (e.g., a rapid heart rate or a drop in temperature), for example, is caused by the release of these neurotransmitters. See, e.g., the on-line article, "Stress and Disease: New Perspectives" (the "Wein Article"), by H. Wein, 2006. Hence, one can gauge the human stress level by tracking a deviations in traditional physiological markers such as body temperature, heart rate, respiration rate, galvanic skin resistance (GSR), hormone concentrations, to name a few. See, e.g., the article, "Physiological Indicators of Stress in Domestic Livestock," by D. C. Lay Jr. and M. E. Wilson, published in the Proc. Int. Anim. Agri. Food Sci. Conf., 2001.

[1] Neurotransmitters are the body's chemicals that carry messages to and from the nerves.

Many diseases or conditions, including anxiety disorders, depression, high blood pressure, cardiovascular disease, certain gastrointestinal diseases, some cancers, and even the process of aging itself, may result from abnormal stress responses. Stress is also believed to be responsible for both the frequency and the severity of migraine headaches, episodes of asthma, and fluctuations of blood sugar in diabetics. Furthermore, scientific evidence indicates that people experiencing psychological stress are more prone to develop colds and other infections than their less-stressed peers. Overwhelming psychological stress (e.g., the event of 9-11) can cause both temporary and long-lasting symptoms of a serious psychiatric illness known as posttraumatic stress disorder (PTSD). See, e.g., the Pan Article.

Unpredictable, uncontrollable, and constant stress may have far-reaching consequence on one's physical and mental health. Stress can begin in the womb and may recur throughout life. One pathological (i.e., abnormal) consequence of stress is a learned helplessness that may lead to clinical depression. In addition, many illnesses (e.g., chronic anxiety states, high blood pressure, heart disease, and addictive disorders) also seem to be influenced by chronic or overwhelming stress.

Monitoring and managing stress can help relieve the side effects of stress. As demonstrated in the Wein Article, while stress is not always bad, too much stress is not good. Stress can help one stay focused, energetic, and alert. In emergency situations, stress can save one's life by bolstering self-defense (e.g., spurring one to slam on the brakes to avoid an accident). Therefore, it is highly desirable to be able to monitor and manage stress—or in general, wellness—using a simple and consistent method. A handheld device, such as a cellular telephone, can be an ideal instrument for implementing such a method, as practically everybody carries one such device at all times.

The study of human stress has involved scientists from different disciplines. Psychologists define stress resulting from emotions (i.e., as positive or negative reactions to situations consisting of events, actors, and objects). See, e.g., "The Cognitive Structure of Emotions" (the "Ortony Book"), A. Ortony, G. L. Clore, and A. Collins, Cambridge University Press, Cambridge, England, 1988. Physiologists demonstrate that high stress level often accompanies large deviations from normal conditions in processes such as heart beat, breathing, sweating, skin temperature, and muscle tension. Ergonomic studies uncover an "Inverted-U" relationship between stress and performance of a task. See, the article, "Worker Participation and Autonomy: A Multilevel Approach to Democracy at the Workplace," B. Gardell, International Journal of Health Services 4:527-558, 1982. Further, facial expressions and gestures have been used to model an affective state recognition system. (See, e.g., the articles (a) "Task-Evoked Pupillary Responses, Processing Load, and the Structure of Processing Resources," J. Beatty, Psychological Bulletin 91:276-292, 1982; (b) "Robot in society: friend or appliance?" C. Breazeal, Proc. Workshop on Emotion-Based Agent Architectures, 18-26, 1999; (c) "Emotion and Sociable Humanoid Robots," C. Breazeal, Int. J. Human-Computer Studies, vol. 59, pp. 119-155, 2003, (d) "Automatic Generation of Multi-Modal Dialogue from Text Based on Discourse Structure Analysis," H. Prendinger, P. Piwek, and M. Ishizuka, Proc. Int. Conf. on Semantic Computing, 2007, pp. 27-36, and (e) "Recognition of Facial Expressions and Measurement of Levels of Interest from Video," M. Yeasin, B. Bullot, and R. Sharma, IEEE Transactions on Multimedia, vol. 8, no. 3, pp. 500-508, June 2006.)

Various other approaches have been developed for recognizing user stress. For instance, stress in a car driver have been detected by measurements of physiological activities (e.g., Electromyograph (EMG), Electrocardiograph (ECG), respiration, and skin conductivity). Examples of such approaches are disclosed, for example, in (a) "Smartcar: Detecting Driver Stress," J. Healy and R. Picard, Proc. 15th International Conference on Pattern Recognition, 2000, (b) "A Decision-Theoretic Model for Stress Theoretic Recognition and User Assistance" ("Liao Article I"), W. Liao, et al., Proc. AAAI, pp. 539-34, 2005; (c) "Toward a Decision-Theoretic Framework for Affect Recognition and User Assistance" ("Liao Article II"), W. Liao, W. Zhong, Z. Zhu, Q. Ji, and W. Gray, International Journal of Human-Computer Studies, 64: 847-873, 2006; and (d) "A reasoning-based framework for car driver's stress prediction" (the Rigas Article"), G Rigas et. al., Proc. 16th Mediterranean Conference on Control and Automation, 2008.

In the article, "Online Stress Detection Using Psychophysiological Signals for Implicit Human Robot Cooperation," P. Rani, J. Sims, R. Brackin, and N. Sarkar, Robotica 20:673-685, 2002, the authors describe applying wavelet decomposition and fuzzy logic techniques to sympathetic and parasympathetic activities of a human heart to determine a stress level. The article, "Monitoring Driver Drowsiness and Stress in a Driving Simulator," M. Rimini-Doering, D. Manstetten, T. Altmueller, U. Ladstaetter, and M. Mahler, Proc. First International Driving Symposium on Human Factors in Driver Assessment, Training and Vehicle Design. 58-63, 2001, describes combining physiological signals and expressive gestures (e.g., eye closure, head movement) to monitor driver drowsiness and stress in a driver simulator).

The variation in body temperature can be measured using inexpensive non-invasive methods. Non-invasive skin temperature measurements overcome the physical discomfort and the difficulty associated with taking measurements from a human body. See, e.g., the article "Development of a Skin Temperature Measuring System for Non-Contact Stress Evaluation" (the "Kataoka Article"), H. Kataoka, H. Yoshida, A. Saijo, M. Yasuda, and M. Osumi, Proc. 20th Annual International Conference of the IEEE Engineering in Medicine and Biology Society 2:940-943, 1998. The skin is kept alive by a minimal blood supply under control of an "internal thermostat," the hypothalamus. In general, "relaxation" increases certain chemicals that increase the blood flow to the skin's surface, causing thereby an increased skin temperature, a drop in core body temperature, and increased heat transfer to the environment. See, e.g., (a) "The Thermosensitivity of the Hypothalamus and Thermoregulation in mammals" J. Bligh, Biological Reviews, vol. 41, no. 3, pp. 317-365, January 2008, and (b) "Principles of Science for Nurses" (the "James Article"), J. James, C. Baker, and H. Swain, published online. On the other hand, colder hands or feet reflect "activation" or "tension" due to activation of the body's sympathetic nervous system to make the muscles tensed and to speed up the heart rate and activities in other vital organs. Changes of 2-4 degrees Fahrenheit can occur in minutes. See, e.g., the James Article referenced above.

It has been observed that stress, whether emotional or physical in nature, can cause sharp fluctuations in body temperature. See, e.g., the articles, (a) "Fundamentals of Nursing: Human Health and Function," R. F. Craven and C. J. Hirnle, 2008, (b) "Thermoregulation," as published in Wikipedia, and (c) "Temperature of a Healthy Human (Body Temperature)," G. Elert, published online.

Research is ongoing on the relationship between a stressful task and skin temperature. One early work is a personal monitor developed to protect workers from heat stress, reported in the article, "Personal Monitor to Protect Workers from Heat Stress" (the "O'Brien Article"), J. F. O'Brien, T. E. Bernard, and W. L. Kenney, Proc. Conf. Human Factors and Power Plants, 1988. The O'Brien Article discloses that the authors developed a small device to be worn by a worker to assess both the body temperature and the heart rate and to alert the worker when either one of the assessments indicates excessive physiological strain. In the Kataoka Article, a facial skin temperature measuring system is reported for non-contact stress evaluation. The article "Development of Flexible Self Adhesive Patch for Professional Heat Stress Monitoring Service," D. G Park, S. C. Shin, S. W. Kang, and Y. T. Kim, Proc. 27$^{th}$ Annual Int. IEEE Engineering in Medicine and Biology Society Conf., September 2005, discloses a flexible self-adhesive patch that could be worn on the chest for professional heat stress monitoring. In Liao Articles I and II, the authors demonstrated a high correlation between fatigue and a temperature measured for stress. In the article, "Wireless Temporal Artery Bandage Thermometer," I. G Finvers, J. W. Haslett, and G Jullien, Proc. Biomedical Circuits and Systems Conference, 2006, Finvers disclosed a bandage-based thermometer for tracking wellness; the bandaged-based thermometer is placed on a patient's temple region of the forehead to measure the core body temperature in a non-invasive manner, to track the patient wellness.

However, these approaches measure single or multiple modalities and are only concerned with tracking the absolute values of physiological quantities. For example, the prior art focuses on mapping stress to an absolute reading of one or more physiological markers (e.g., the absolute temperature, absolute heart rate).

In addition to stress modeling, many articles disclose modeling affective states recognition. In addition to the Liao Articles I and II, such articles include (a) "Lifelike pedagogical Agents and Affective Computing: An Exploratory Synthesis," C. Elliott, J. Rickel, and V. W. Friesen, Proc. Artificial Intelligence Today. Lecture Notes in Computer Science (1600), Springer Verlag, 1999, (b) "To feel or Not to Feel: The Role of Affect in Human-Computer Interaction," E. Hudlicka, International Journal of Human-Computer Studies 59:1-32, 2003, and (c) "Probabilistic Combination of Multiple Modalities to Detect Interest," A. Kapoor, R. Picard, and Y. Ivanov, Proc. International Conference on Pattern Recognition, 2004.

Recently, probabilistic-reasoning approaches have been applied to model user affects. The probabilistic-reasoning techniques are concerned with graphical models, such as hidden Markov models (HMM), Bayesian network (BN) and Influence Diagram (ID). See, e.g., Liao Article I. The book "Affective Computing" (the "Picard Book"), R. Picard, Cambridge University Press, Cambridge, England, 1997 discloses using an HMM to model the transitions among three affective states: interest, joy and distress. HMMs, however, lack the capability of representing dependencies and semantics at different levels of abstraction for affect modeling. The article "Active Affective State Detection and User Assistance with dynamic Bayesian Networks," X. Li and Q. Ji, IEEE Transactions on Systems, Man, and Cybernetics, Part A: Systems and Humans, 2004, discloses using a dynamic BN to recognize user affect and provide user assistance. However, this user assistance function is triggered by some pre-determined thresholds since a BN does not have an explicit representation for decision making (user assistance).

Likewise, the article "Probabilistic Assessment of User's Emotions in Educational Games," C. Conati, Journal of Applied Artificial Intelligence, 16:555-575, 2002, discloses using a dynamic decision network to monitor a user's emotions and engagement during the interaction with educational games. However, their work uses only bodily expressions related features and suffers from a lack of validation. The dynamic Bayesian network (DBN) framework cited by Liao Article I uses dynamic inference and sequential decision making techniques to unify stress recognition with user assistance, utilizes evidences from multiple modalities, and is validated in a real-time system with theories of psychology.

The article "Development stress monitoring system based on personal digital assistant (PDA)," M. H. Lee, G Yang, H. K. Lee, and S. Bang, Proc. Engineering in Medicine and Biology Society, September 2004, pp. 2364-2367, discloses a stress monitoring feature in a wireless handheld device (e.g., a PDA). Lee monitors more than one physiological quantity, using an electrode to measure skin temperature. Lee merely tracks the skin temperature and infers stress levels based on the variation in the absolute reading of the temperature. Similarly, the article "A PDA based Ambulatory Human Skin Resistance Measuring System," Q. Fang et. al., Telehealth, 2005, discloses a PDA-based ambulatory human skin resistance measuring system.

Only Liao Articles I and II and the article by Rigas et. al. disclose state-of-the-art temporal Bayesian network (TBN) frameworks for monitoring fatigue and stress. These frameworks are all multiple-modality frameworks that impose both hardware and computational burdens not suitable for implementing on a wireless handheld device. Further, while Liao Articles I and II provide a framework for inferring fatigue and stress using only mental stressors, the article by Rigas et. al., discloses a stress detection technique exclusively for a driving test.

In summary, the prior art teaches a number of stress-tracking models, which consider only instantaneous measurements of a physiological entity (e.g., the instantaneous body temperature, or the instantaneous heart rate).

SUMMARY OF THE INVENTION

The present invention provides techniques for wellness self-monitoring that can be implemented in a handheld device (e.g., a cellular telephone). In one embodiment, fluctuations in one or more biometrics (e.g., body temperature, heart rate, etc.) are computed iteratively. The present invention provides algorithms for detecting the biometric fluctuations, thus aiding in effective wellness management.

The present invention also provides a probabilistic inference algorithm that monitors fluctuations in one or more biometrics during an activity, so as to perform effective inference regarding the state of human stress associated with that activity in an efficient and timely manner. Stress state recognition during an activity is achieved through dynamic probabilistic inference using sensory data from multiple-modality sensors.

Generally speaking, a method of the present invention for detecting a subject's stress level associated with an activity includes (a) connecting the subject to a sensor that senses a value of a biometric; (b) during the activity, (i) repeatedly sensing the value of the biometric over each of a plurality of time windows; and (ii) computing, for each time window, a deviation in the sensed values of the biometric; and (c) detecting the stress level based on the computed deviations. In one implementation, the value of the biometric is a skin temperature measurement. The method may be implemented as an application in a wireless handheld device, such as a cellular telephone.

According to one embodiment of the present invention, deviations in skin temperatures are tracked to infer stress levels in humans. Specifically, an algorithm iteratively tracks the fluctuations in skin temperatures during different activities so as to compute a wellness index based on stress levels. The techniques and the algorithms of the present invention may be implemented on a handheld device (e.g., a cellular telephone) without requiring expensive or dedicated hardware. Thus, the present invention provides a cellular telephone user, for example, an application to monitor stress levels easily and consistently. The present invention discerns stress levels in humans during different activities based on iterative differences in skin temperature. In addition, a model of the present invention takes into account the ambient temperature while computing the differences in skin temperature recursively.

Unlike the approach taken in Liao Article I, the present invention generates "evidence" and "inference" models from tracking deviations in temperature and applies an iterative Bayesian-based algorithm on these models to predict stress states. An "emotional" mouse, which tracks three physiological parameters (i.e., heart rate, skin temperature at the base of the palm, based on the sensor placement on the mouse and GSR) corroborates the model of Liao Article I. In one embodiment, the skin temperatures at the index and middle fingers, palm, and forehead are measured to corroborate the predictions of an iterative wellness monitoring algorithm of the present invention.

The present invention provides stress recognition and tracking based on measurements of differences in a physiological activity (e.g., the skin temperature).

In one embodiment, the present invention is simple enough to be implemented using only features or sensors already existing or available on a conventional cellular telephone, so that monitoring of stress levels may be implemented using only software, without requiring additional hardware for stress detection.

Thus, a real-time human stress monitoring system is provided for recognizing stress during a daily lifestyle, using an iterative deviations method (IDM). The IDM provides a piece-wise constant stress classifier, where the transition regions were indicative of a change in the engagement of a task.

The present invention further provides an even more accurate stress state tracking using a temporal Bayesian network (TBN) based stress tracking algorithm, which accounts for uncertainties in the 'events' or tasks and prior probabilities (i.e., the user's prior stress states before performing the current task). The TBN-based algorithm tracks stress state transitions closely, at a higher cost of computationally intensity when, for example, multiple modalities are tracked. The algorithm may require training data to find or refine the conditional probabilities used in the model.

According to one embodiment of the present invention, a simple 'single-modality' TBN framework detects user-stress that predicts affective states, based on a time-series of skin temperature measurements. The probabilistic framework performs stress recognition and monitoring based on variations in biometrics during emotional, visual, and physical event-based stress stimuli. The probabilistic framework may track multiple-modalities to infer human stress, using a single biometric, so as not to require hardware or computational burden on implementation in a wireless device (e.g., a cellular telephone).

According to one embodiment of the present invention, an inference algorithm based on the TBN framework relies on a single biometric, measured over temporal windows of observations of the biometric (i.e., skin temperature measurements). Despite being a single-modality sensor tracking, an algorithm of the present invention can make an inference after observing many samples, and thus reduces the possibility of false alarms resulting from transient fluctuations in the biometric. Experimental results show that reliable stress state recognition and tracking are achieved using a statistical algorithm of the present invention. The simplicity of the technique (i.e., the single-modality tracking) enables implementation on a handheld device (e.g., a cellular telephone) without additional hardware.

The present invention is better understood upon consideration of the detailed description below in conjunction with the accompanying drawings.

DETAILED DESCRIPTION OF THE PREFERRED EMBODIMENTS

Figure 1:
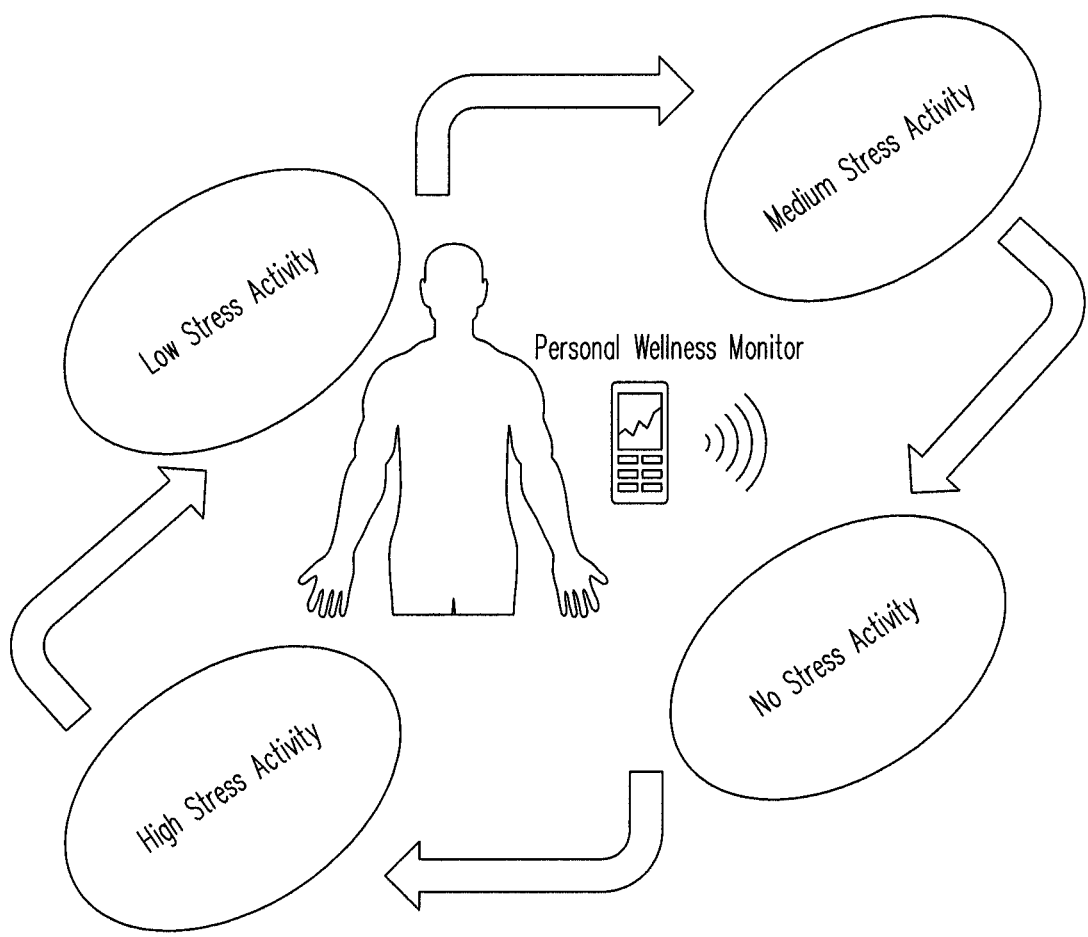
FIG. 1 illustrates a model that classifies activities and roles of an ordinary working person engaged in activities that are broadly classified as normal, low-stress, moderate-stress and high-stress.

"Wellness monitoring" is still a nascent concept. As many quantifiable measurements of wellness are still being developed, an intelligent monitoring system thus remains a challenge. The present invention relates a variation in biometrics in humans (e.g., skin temperature, heart rate) with wellness. Wellness may be expressed, for example, as such quantities as stress levels and levels of fatigue. Particularly, according to one embodiment of the present invention, skin temperature is related to stress levels associated with an activity. Because the glands that are responsible for "sympathetic activity" are plentiful at ends of the limbs ("extremities"), changes in blood flow that causes fluctuations in skin temperature around the body are most pronounced at the extremities. For a discussion of sympathetic activity at the extremities, see the article "Job Demands, Job Decision Latitude and Mental Strain: Implications for Job Design" (the "Karasek Article"), R. A. Karasek, Administrative Science Quarterly 24:285-308, 1979. On the hand itself, for example, cold thresholds are smallest on the dorsal surface and largest on the finger tips and pads of the palms. See, e.g., "Peripheral Neural Determinants of Temperature Discrimination in Man: A Correlative Study of Responses to Cooling Skin," K. O. Johnson, I. D.-Smith, and C. LaMotte, J. Neurophysiology, vol. 36, pp. 347-370, 1973. In general, as warm thresholds are twice as large as the cold thresholds, the better a site is at detecting cold, the better it is at detecting warmth. See, e.g., the article "Temperature Sensitivity of the Body Surface Over the Life Span" (the "Stevens Article") J. C. Stevens and K. C. Choo, Somatosensory and Motor Research, vol. 15, pp. 13-28, 1998. Data showing a distribution of temperature sensitivity in human hands may be found, for example, in the article "Warm or Cool, Large or Small? The Challenge of Thermal Displays" (the "Jones Article") L. A. Jones and H.-N. Ho, IEEE Trans. On Haptics, vol. 1, no. 1, pp. 53-70, January-June 2008, and in the Stevens Article. Therefore, in one embodiment, based on a bar-chart in FIG. 2 of the Jones Article and data from the Stevens Article, the index fingers are selected for recording temperature measurements.

The present invention monitors the state of wellness in a human, as the human performs his/her daily routines. The inventors believe that sharp and rapid fluctuations in biometrics directly correlate with a drift from a normal state of wellness. Specifically, the present invention tracks variations in skin temperature to assess stress levels associated with an activity that are indicative of wellness. According to one embodiment of the present invention, simple stress detection algorithms are provided based on the iterative deviations method (IDM) and the dynamic Bayesian networks (DBN). The models and tracking algorithms of the present invention are sufficiently simple as to allow implementation in a handheld device, such as a cellular telephone, or a PDA. Although the present invention is described herein using single-modality tracking algorithms, multiple-modality tracking algorithms may be provided within the scope of the present invention.

Mathematically, let $P_a$ be a base line or ambient value of the biometric that is monitored, $P_n$, and $P_{n+1}$ be the instantaneous biometric measurements at times $t_n$, and $t_{n+1}$, respectively, for $n=1, \ldots, N$. Then, the deviation over the samples in the biometric $\Delta P_n$ is provided by the following equation:

$$\Delta P_k = \max_n (P_a - P_n) - \min_n (P_a - P_n), \text{ for } k = 1, 2, \ldots \quad (1)$$

FIG. 1 shows a model of the activities and roles of an ordinary working person engaged in activities broadly classified into normal, low-stress, moderate-stress, and high-stress. The inventors believe that the variations in the measurements of one or more biometrics (e.g., skin temperature) are markedly different for the distinct activities. The order in which the various activities are performed and the duration of each activity are believed to affect the measured values of the biometrics. The present invention may implement a model and one or more tracking algorithms on a handheld device, such as a cellular telephone. Consequently, a cellular telephone user can monitor his/her stress levels periodically and can conform his/her lifestyle accordingly. A cellular service may provide timely and appropriate user assistance based on the cellular telephone user's "wellness state." For example, a cellular telephone operator may respond to a detected wellness emergency condition without an express request from the user.

Figure 2:
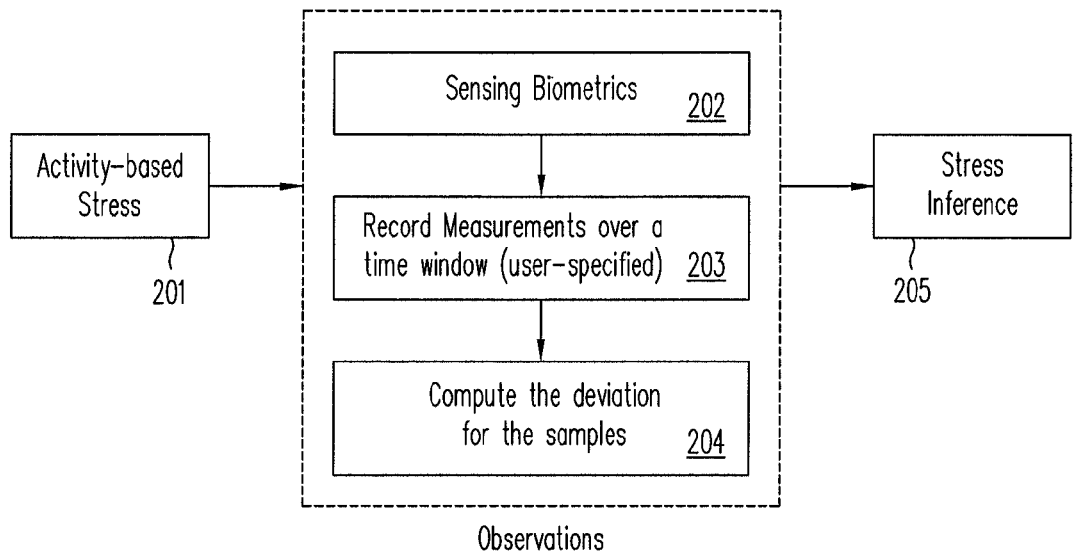
FIG. 2 illustrates a model of the present invention for computing variations in biometrics, in accordance with the present invention.

A stress model of the present invention based on measured and computing variations in biometrics is illustrated by the flow chart of FIG. 2. The model is suitable for a wellness mobile application, with which a cellular telephone user keep tracks of his/her stress level based on his/her daily activities. As many existing "smart phones" have installed biometric sensors, the stress model of FIG. 2 may be implemented in smart phones currently available or available in the near future. As shown in FIG. 2, step 201 indicates the beginning of an activity for which stress level is measured. Steps 202-204 are repeated periodically over time windows at times $t_1$, $t_2$, $t_N$. At steps 202-203, one or more selected biometrics are measured over each time window. At step 204, a deviation for each measured biometric is computed (see below for a detailed discussion of the deviation computed). At step 205, a stress detection or inference algorithm evaluates the computed deviations to detect a stress level and appropriately report any detection.

Figure 3:
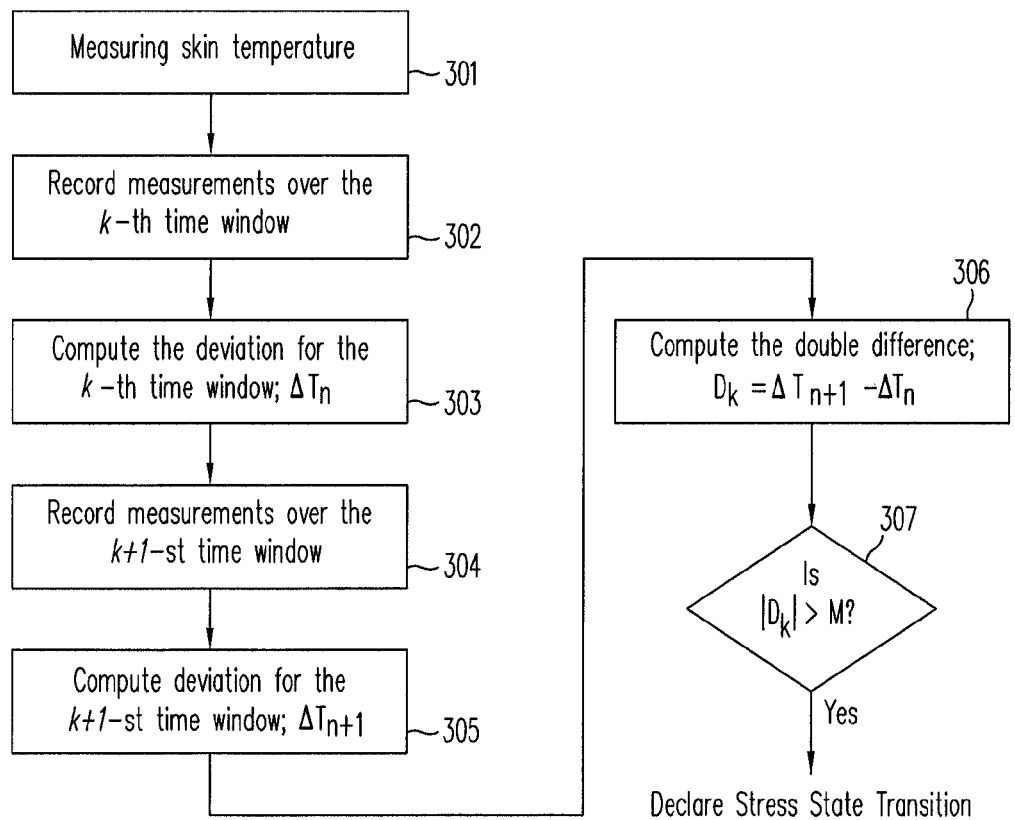
FIG. 3 is a flow chart that illustrates a method for tracking stress levels of a user using a series of temperature measurements $\Delta T_k$ over time, in accordance to one embodiment of the present invention.

FIG. 3 is a flow chart that illustrates a method for tracking stress levels of a user using a series of skin temperature measurements $\Delta T_k$ over time, in accordance to one embodiment of the present invention. At step 301, a temperature sensor is activated. Periodically (e.g., at each of steps 302 and 304), a number (N) of temperature measurements are made over a time window. Let $T_a$, $T_n$, and $T_{n+1}$ be the ambient temperature, and the instantaneous temperature readings (e.g., skin temperature) of a user at times $t_n$, and $t_{n+1}$, respectively, for n=1, ..., N. Then, a deviation in the user's skin temperature ($\Delta T_k$) is computed iteratively using the following equation for each time window (e.g., steps 303 and 305):

$$\Delta T_k = \max_n (T_a - T_n) - \min_n (T_a - T_n), \text{ for } k = 1, 2, \ldots \quad (2)$$

In this embodiment, the parameter monitored is a deviation in the temperature samples of the user, and not the absolute temperatures. Further, the IDM model captures both increase and decrease in temperature, and also takes into account the ambient temperature. In one experiment conducted by the inventors, the ambient temperature was kept constant. However, the model can be easily modified to absorb any variation in the ambient temperature during an activity. For example, if the cellular telephone user moves from indoors to outdoors during an activity, the model may account for the change in ambient temperature by recording all temperatures relative to the contemporaneous ambient temperature. Temperature readings of the subject (e.g., skin temperature) may be measured at the extremities (e.g., index finger), palm, or the forehead.

The IDM computes the deviations to monitor the stress state. From the experiments conducted, described below, the inventors showed that a sharp fluctuation in deviation $\Delta T_k$ over successive measurement windows is indicative of a change in workload, which can be mapped to a different pre-defined stress index. The wellness of a cell telephone user can be inferred from this stress index. The quantity $|\Delta T_{k+1} - \Delta T_k| = DD_k$, computed at step 306, represents a change in deviation between successive measurement windows, is referred to as the Deviation Difference (DD). Under one method of the present invention, a stress state transition is declared when $|DD_k| > M$, where $M \geq 1$ is a predetermined threshold (step 307). Based on activity-based stress experiments, the inventors found that in general, $M \geq 1.5$ was a reliable state transition indicator.

Figure 4:
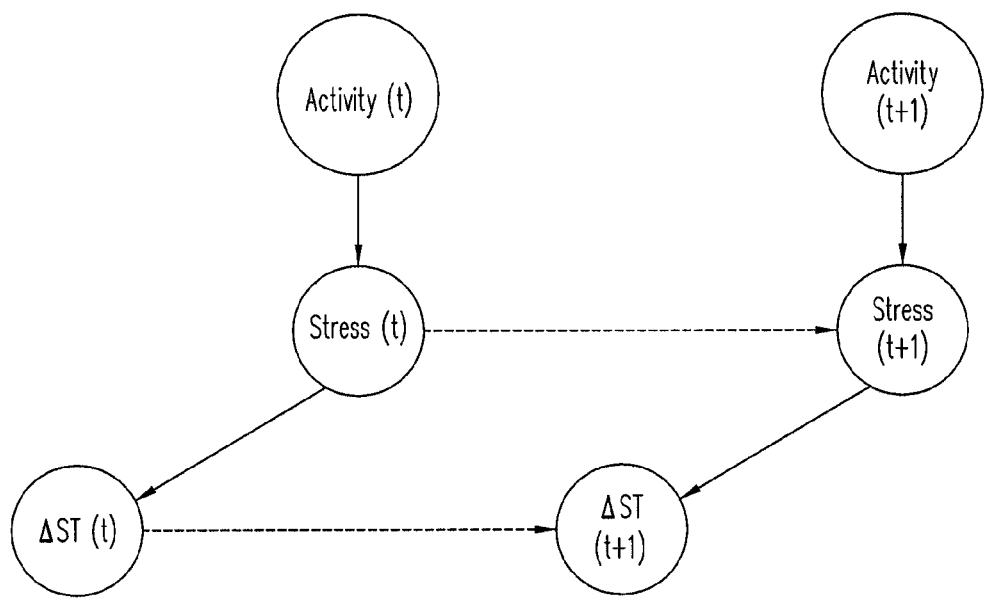
FIG. 4 is a schematic diagram illustrating a dynamic Bayesian Network (DBN).

Alternatively, one can track and infer the wellness of a cellular telephone user using the dynamic Bayesian networks (DBN), such as suggested by Liao Article I. Unlike Liao Article I, the present invention uses a difference in a biometrics (e.g., skin temperature). While multiple-modality model for inferring stress was disclosed in Liao Article I, Liao Article I determines stress levels using absolute values of physiological biometrics. FIG. 4 is a schematic diagram illustrating a DBN. As illustrated in FIG. 4, a "static" BN renders a time-snapshot of the stress state that is activity-induced (e.g., stress state 401-$t$ at time t is induced by activity(t) and stress state 401-($t$+1) at time t+1 is induced by activity(t+1)), by observing a difference in skin temperature. Over a time interval, we have a "dynamic" BN to track the state transitions of stress (e.g., state transition 402-$t$ at time t and stress transition 402-($t$+1) at time t+1), In this embodiment, the stress transition model is the Bayesian probability $p(S_{t+1}|S_t)$ where $S_t$ is the stress level at time t. The detection model is defined as the Bayesian probability $p(O_t|S_t)$, where $O_t$ is the deviation in skin temperature at time of snapshot t (i.e., $\Delta ST(t)$ in FIG. 4). The inference model is provided by the Bayesian probability $p(S_t|O_{1:t})$. The Bayesian approach computes $p(S_{t+1}|O_{1:t+1})$ iteratively using $p(S_t|O_{1:t})$. Using the Chapman-Kolmogorov equation, we have $$p(S_t | O_{1:t}) = \frac{p(S_t | O_t) p(S_t | O_{1:t-1})}{p(O_t | O_{1:t-1})}. \quad (3)$$

The model was validated by experiment data.

Validating a stress monitoring system is difficult because there is not a uniformly accepted reference ("ground-truth") for quantifying stress. Users' self-reports have been found to be erroneous and unreliable. The existing results from psychological studies show that occupational stress is affected by the workload. See the Karasek Article, and the article, "Testing the Three-Factor Model of Occupational Stress: The Impacts of Demands, Control and Social Support on a Mail Sorting Task" (the "Searle Article"), B. J. Searle, J. E. Bright, and S. Bochner, Work and Stress 13:268-279, 1999. In the inventors' experiment, the approach of Liao Article I is adopted, which uses workload (demand or engagement) to represent user stress level. In the inventors' experiment, workload is specific to an activity (i.e., workload is measured by the amount of attention and effort required to complete the activity). In one experiment, to change a subject's stress level, the subject's activity is changed.

Figure 5:
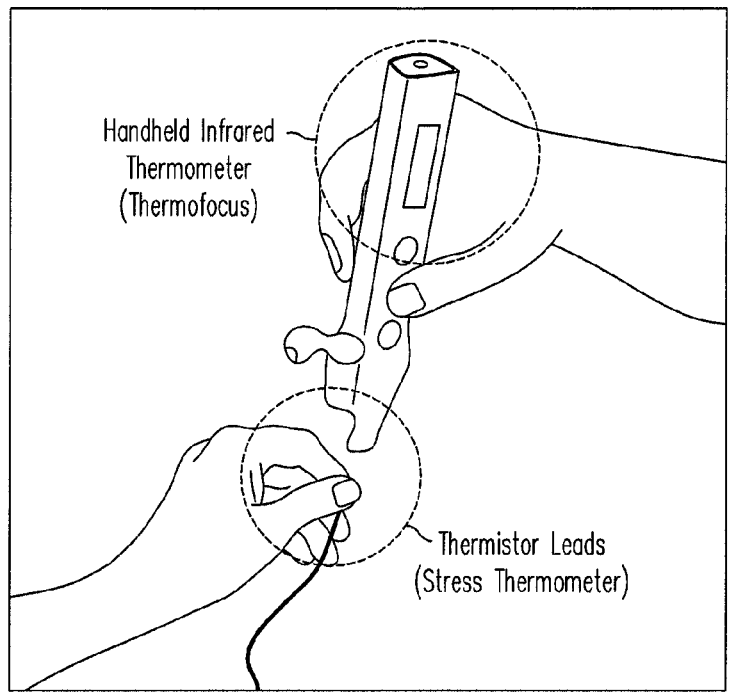
FIG. 5 shows an experimental setup used in the inventors' experiments.
Figure 5:
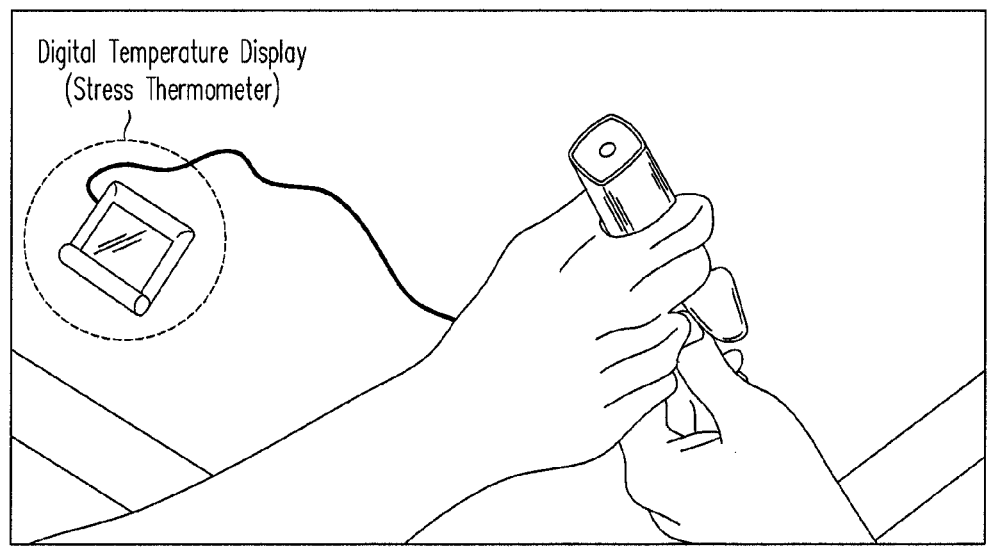

FIG. 5 shows an experimental setup that was used in the inventors' experiment. As shown in FIG. 5, in order to measure the temperature of the subjects, a Kidz-Med Thermofocus Non-Contact Infrared Clinical Thermometer was used. (A description of this thermometer can be found online. The subject of an experiment was also connected to a commercial stress thermometer (see, http://bio-medical.com), which provided a reference to typical accuracy and sensitivity of an off-the-shelf product. As shown in FIG. 5, the subject was connected to electrical leads of the commercial stress thermometer, which provides a digital display of a measurement.

In the inventors' experiment, the subject responded to three types of situations under pressures that are believed to cause stress ("stressors"). Stressors are often thought of as undesirable activities (e.g., an exhausting work schedule or a rocky relationship). However, anything that puts high demands on a person or forces the person to adjust can be stressful, even when the events are considered desirable (e.g., a wedding, a purchase of a house, starting college, or receiving a promotion). Stress appears to depend, at least in part, on one's perception. One person's stressful event may be harmless to another; or even enjoyable. For example, a long morning commute may make some people anxious and tense because of the worry of being late to work. To another, however, such a trip may be relaxing because he/she enjoys listening to music while he/she drives. The inventors therefore designed stressors for which cause (activity) and effect (fluctuations in temperature indicative of stress) in the participants can be isolated.

As a first step of the inventors' experiment, a single-modality is used to infer the wellness of a person. The stressors varied according to the extent to which the participant was engaged, and they also isolated the cause (i.e., stress associated with the activity) and the effect (i.e., fluctuations in the skin temperature, in this case). The experiment validated the hypothesis of the stress model described in conjunction with FIGS. 1 and 2.

Figure 6:
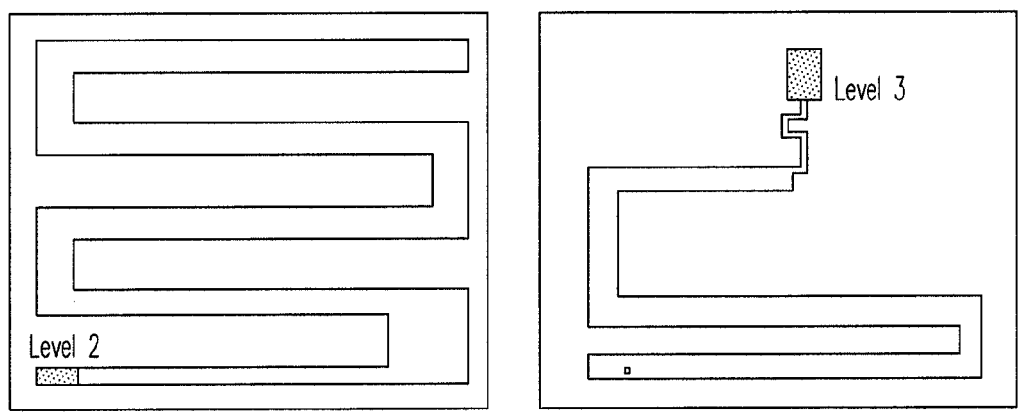
FIG. 6 shows two screenshots (a) and (b) of the Scary Maze Game.

(a) Shock Stressor—each user was asked to play the Scary Maze Game on the computer. A description of the game is found online. In the game, the subject's task was to guide a dot (using a mouse) through a scary maze to a red square, without hitting the walls of the maze This game ranks as one of the scariest games online, and has durations of 1-3 minutes, depending on the user's skill level. Clearing the maze at level 2 is considered moderately difficult, but level 3 requires significantly more skill, and level 4 requires even greater skill. Two screenshots of the game are shown in FIG. 6. In the inventors' experiment, 20 male and 11 female employees of DOCOMO Communications Laboratories USA Inc., Palo Alto, Calif, ("DOCOMO Labs") participated. The subjects underwent a series of temperature measurements (on the index finger, thumb, palm, and forehead) just before, during, and after completing the task. A total of 15 skin temperature measurements were made for each test subject. The off-the-shelf stress thermometer was also read to measure each subject's stress level.

(b) Math Stressor—The Math Stressor had three segments:
  (i) In the first segment, the subjects were asked to iteratively subtract the prime number 13 from 967 until they were left with a number less than 13. The subjects performed this recursive subtraction mentally without aid of pen or paper, and announced aloud the result of each subtraction. When an error was made, the subject was asked to restart from the last correct number. Each subject was allowed five minutes to complete his/her task, and a prize was promised to the person who was to complete the task with fewest errors and finishes within the shortest time.
  (ii) In the second segment, the subjects performed the same recursive subtraction as in the first segment, except that a loud buzzer is sounded after every minute, until the last minute, when buzzers went off after every 20 seconds. The sudden buzzers were intended make the activity even more stressful.
  (iii) In the third segment, the subjects performed the same recursive subtraction as in the second segment, except that the subjects were required to announce each result to the beats of a metronome. The beats of the metronome were altered to vary the engagement of the subject.

18 male and 14 female employees of DOCOMO Labs participated in this experiment. The subjects underwent skin temperature measurements (on the index finger, thumb, palm, and forehead) just before, during, and after completing the task. 20 temperature readings were taken for each segment, and a total of 60 readings were taken for the whole activity. The off-the-shelf stress thermometer measured the stress level.

c) Public Speaking Stressor—This stressor was designed based on studies which show that the fear of public speaking is as stressful as the fear of death. See, e.g., the article "The Fear of Public Speaking," H. Gottlieb, 2004, published online. A recent study shows that a person who is among those who fear speaking in public most becomes more anxious—not less—as his/her public speech progresses. In fact, instead of feeling relieved at the end of the speech, the subject becomes even more anxious. See, e.g., the article "Fear of Public Speaking Hardwired," D. DeNoon, 2006, published online. 10 male and 3 female employees of DOCOMO Labs participated in this experiment. The speakers underwent a series of skin temperature measurements (on the index finger, thumb, palm, and forehead) just before and after making a three-minute assigned presentation. 10 readings were taken for each speaker about two hours before his/her presentation, 15 readings were taken just before his/her turn, and 10 readings were taken right after he/she completed the presentation. The off-the-shelf stress thermometer measured the stress level.

In order to study the relation between the temperature measurements and stress, the inventors used the exploratory data analysis (EDA) and the confirmatory data analysis (CDA). The EDA is an approach to analyze data for formulating hypotheses that are worth testing; this approach thus complements the conventional tools of statistics used for hypothesis testing. One of the principle graphical tools used in EDA is the box plot. The CDA uses statistical techniques, such as the ANOVA (analysis of variance) test, correlation analysis, Friedman's test, and the Kruskal-Wallis test. The ANOVA, Friedman, and Kruskal-Wallis tests were used to determine if the mean of the measurements according to activity differed when the measurements were grouped by stress levels. While the ANOVA test assumes that the measurements are independent and conforming to a normal distribution, the other tests are non-parametric versions of the ANOVA test for measurements that are distributed in a continuous distribution that is not the normal distribution. The inventors computed the probability of the null hypothesis using the three different tests to validate the model, classifying the stress levels as low, moderate, and high stress levels.

Figure 7:
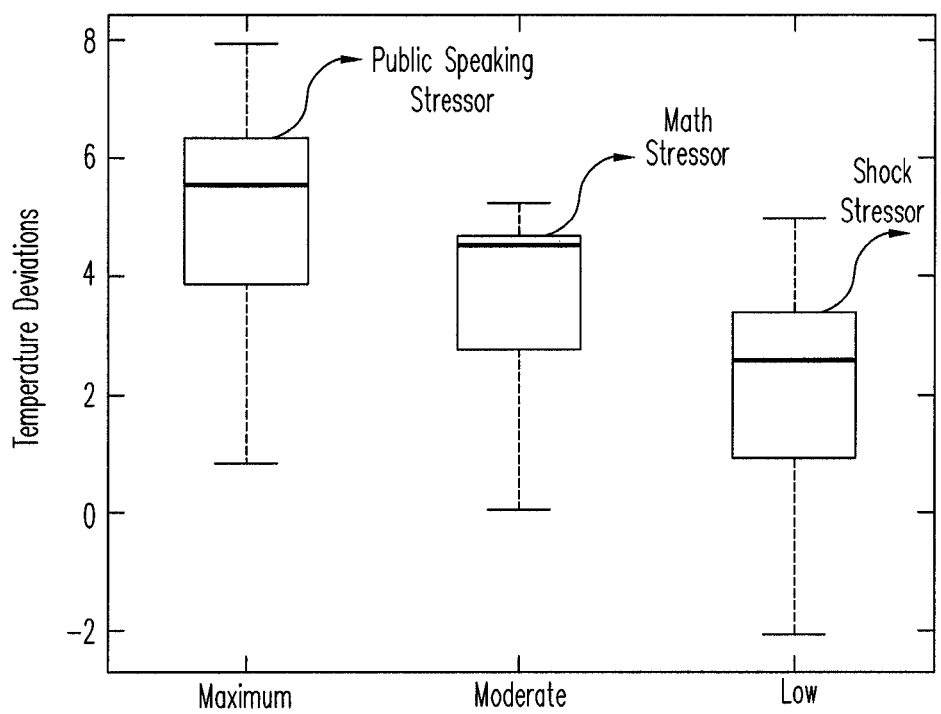
FIG. 7 is a box plot which compares three groups of temperature deviations corresponding to the three stressors.

FIG. 7 is a box plot which compares three groups of temperature deviations corresponding to the three stressors. The box plot displays differences between populations without making any assumptions as to whether or not the underlying statistical distribution is non-parametric. The spacings between the different parts of the box indicate the dispersion (spread) and skew-ness in the data, and identify outliers. As can be seen from FIG. 7, the "group" mean for each stressor is markedly different from the "whole sample" mean. This result establishes the existence of a correlation between each stressor and the variation in the skin temperature measured. The exact correlation, however, is not established by the limited data. In statistics, the p-value is the probability of observing a result at least as extreme as the test statistic, assuming the null hypothesis is true. The p-values in the inventors' experiment were 0.0253, 0.0092, and 0.006, using the ANOVA, Friedman and Kruskal-Wallis tests for 30 subjects for the three stressors described above. Since the p-value is less than 0.05, each test result may be accepted as statistically significant, thus validating the proposition that stress level is sensitive to the workload (i.e., the activities are stress-inducing activities). The low p-value show that the ANOVA, Kruskal-Wallis and Friedman tests all agree with each other.

The correlation coefficients computed over time between each individual measurement and stress level reveal how the measurement varied as the stress underwent changes. The computed coefficients show that the skin temperature variations were closely correlated to the stress level of the activity.

Figure 8:
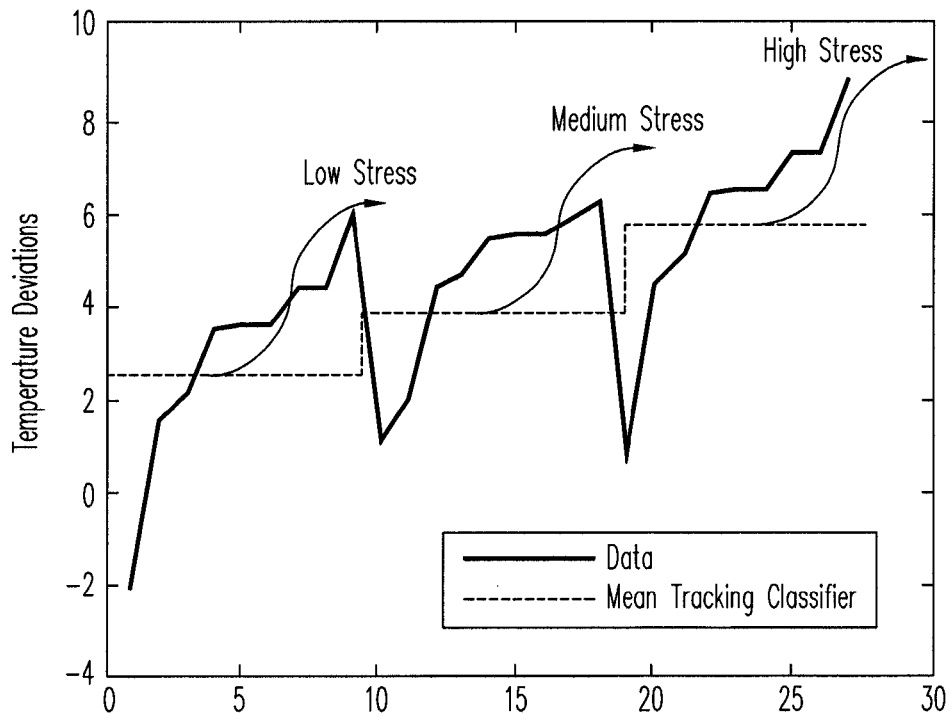
FIG. 8 demonstrates a simple stress classifier that is based on iteratively computing and tracking the instantaneous variations in a subject's skin temperature, in accordance with one embodiment of the present invention.

FIG. 8 demonstrates a simple stress classifier that is based on iteratively computing and tracking the instantaneous variations in a subject's skin temperature, in accordance with one embodiment of the present invention. FIG. 8 plots temperature deviations during performance of the three stressors (i.e., the three activities). The first portion of the curve (labeled "low stress") corresponds to the subject under the shock stressor, the second portion (labeled "medium stress") corresponds to the subject under the math stressor, and the third portion (labeled "high stress") corresponds to the subject under the public speaking stressor. From FIGS. 7 and 8, both the maximum and the minimum temperature deviations for each group increase with the stress-level associated with the activity. For example, after the participant completed the first activity (i.e., Shock Stressor), the mean skin temperature deviation was about 1.5 degrees Fahrenheit. However, the mean temperature deviation increased to about 3.8 degrees Fahrenheit by the time the subject completed the second activity (i.e., Math Stressor). Hence, the relative change in skin temperature caused by the activity is slightly more than 2 degrees Fahrenheit. This result indicates that a change in the stress level of the participant is a function of the activity performed. Therefore, by tracking the means of the temperature deviations, it is possible to measure a stress level.

Figure 9:
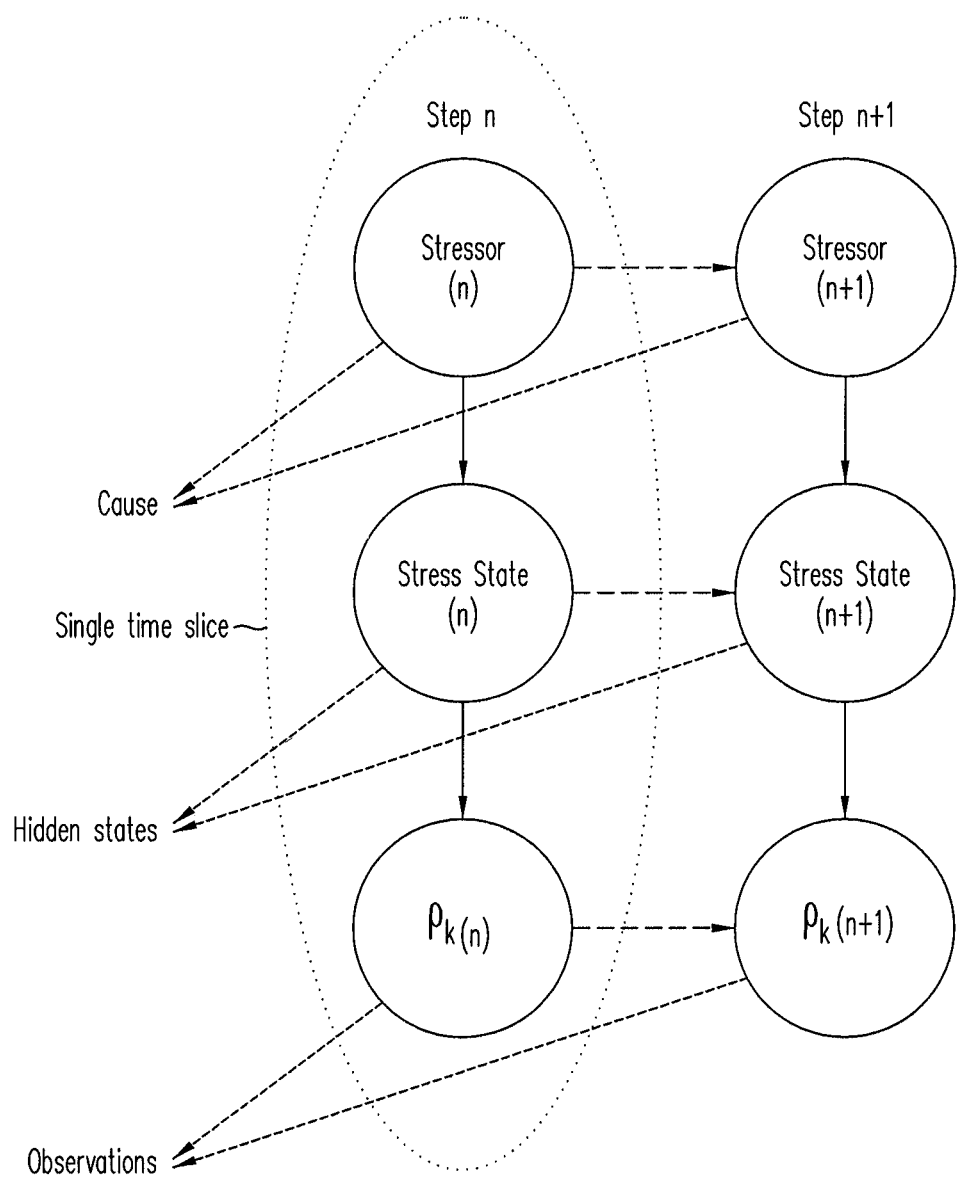
FIG. 9 shows a time-state extension of a single time slice BN; the time-state extension results in a TBN.

According to a further aspect of the present invention, the associations between the different experiments that were conducted, and the participants' stress levels may be modeled as a TBN. A single-time slice BN is a graphical model, which represents conditional dependencies between any set of random variables. A generic TBN is a three-level architecture consisting of event variables, hidden state variables, and the observable variables. FIG. 9 illustrates extending a time-state of a single-time slice BN to result in the TBN. As shown in FIG. 9, each time slice (e.g., time slice for t=n) includes a cause (e.g., cause 901, corresponding to one of the events, such as a stressor), a stress state (e.g., stress state 902, corresponding to a state variable which may not directly observable), and an observation (e.g., observation 903, corresponding to an observable variable, such as a deviation in skin temperature). Using probabilistic associations between different sets of variables and the observable variables (i.e., skin temperature samples), the present invention accurately infers and tracks the state transitions of the hidden stress states. The inferred state transition provides the BN time slice for time t=(n+1).

Formally, the three variables of interest for the present invention are task, $A = \{A_1, \ldots, A_N\}$, stress states, $S = \{S_1, \ldots, S_N\}$, and the deviations in various temporal windows during which temperature measurements, $\rho = \{\rho_1, \ldots, \rho_N\}$ are made. Each TBN time slice models a stress-inducing task, which causes an 'observable' change (e.g., a fluctuation in skin temperature). The joint probability distribution of the TBNs is provided by:

$$p(A, S, \rho) = p(A_0) \prod_{k=1}^{N} p(A_k | A_{k-1}) \prod_{k=1}^{N} p(S_k | A_k) \prod_{k=1}^{N} p(S_k | S_{k-1}) \prod_{k=1}^{N} p(\rho_k | S_k). \quad (4)$$

where $A_0$ is the initial state of the activity, and we assume p($A_0$) to be unity.

In one embodiment, a TBN-based stress tracking algorithm includes a stress transition model expressed as $p(S_{k+1}|S_k)$, where $S_{k+1}$ and $S_k$ are the stress states at steps k+1 and k, respectively. The detection model is $\rho(\rho_k|S_k)$, where $\rho_k$ is the observation at time k (i.e., the deviation in the temperature measurements of temporal window k). In that embodiment, each temporal window has duration of 4 minutes and includes 20 samples. The detection model is provided by conditional probabilities that are obtained empirically. Tables 1 and 2 show conditional probabilities obtained from one experiment, described in further detail below.

The inference model, which is $p(S_k|\rho_{1:k})$, is updated in a recursive fashion at each step. At step k=0, the inference model reduces to $p(S_0)$. In one embodiment, the initial stress state, $S_0$, is low (e.g., ~0.1), constructed based on the responses from the 'truthful' test-taker. These parameters are usually determined empirically or taken from existing literature, which includes Liao Article II, the Rigas Article, the Ortony Book, the Picard Book, and the following articles: (a) "Crew Factors in Flight Operations XIII: A Survey of Fatigue Factors in Corporate/Executive Aviation Operations" (the "Rosekind Article"), M. R. Rosekind et al., National Aeronautics and Space Administration NASA/TM-2000-209610; (b) "Fatigue Countermeasures in the Railroad Industry—Past and Current Developments" (the "Sherry Article"), P. Sherry, Counseling Psychology Program, Intermodal Transportation Institute, Denver, and (c) "Active and Dynamic Information Fusion for Facial Expression Understanding from Image Sequence" (the "Zhang Article"), Y. Zhang and Q. Ji, IEEE Trans. Pattern Analysis and Machine Intelligence, vol. 27, no. 5, pp. 699-714, 2005.

Figure 10:
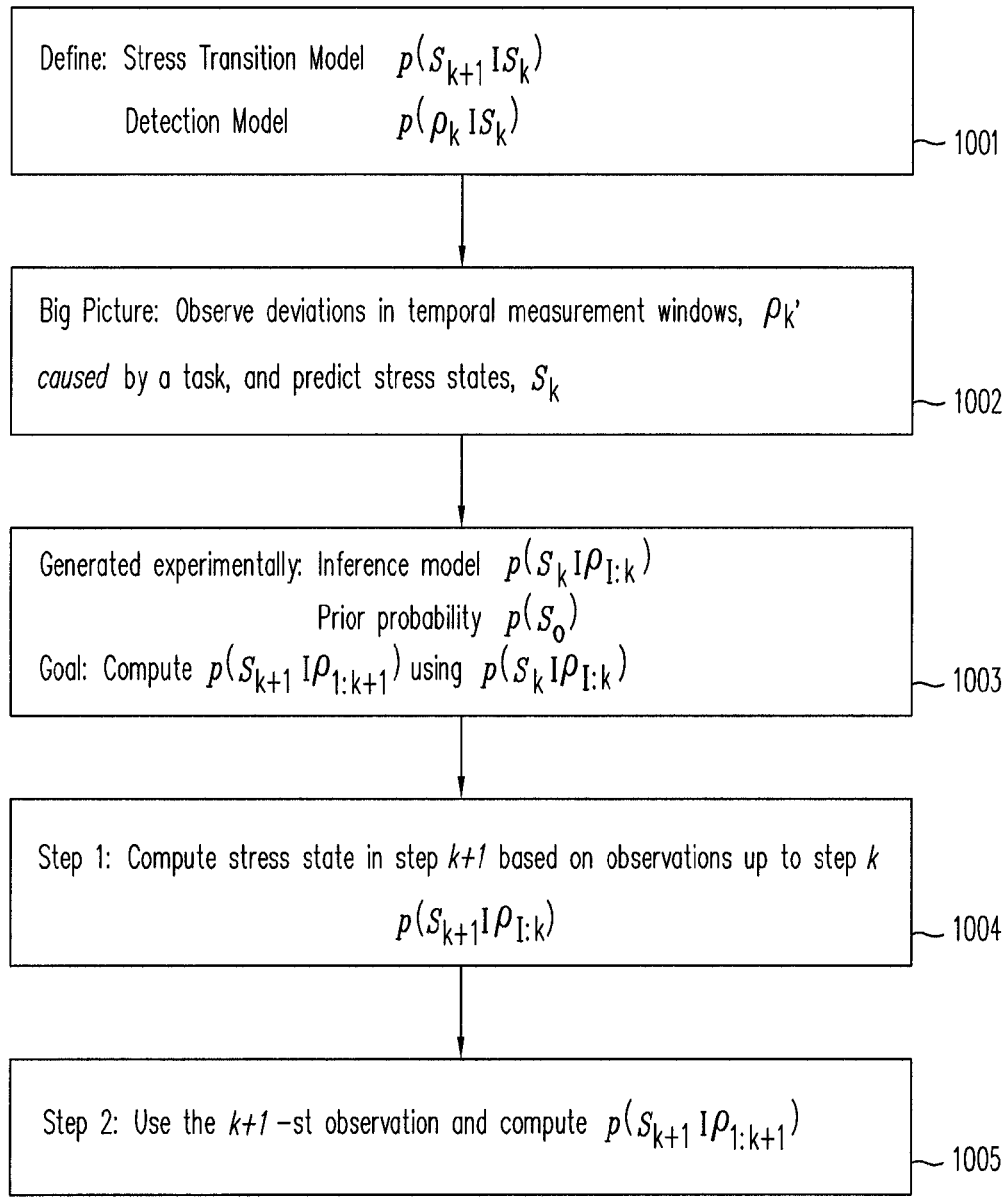
FIG. 10 is a flow chart illustrating stress-tracking algorithm 1000, in accordance with one embodiment of the present invention.

FIG. 10 is a flow chart illustrating stress-tracking algorithm 1000, in accordance with one embodiment of the present invention. As illustrated in FIG. 10, at step 1001 (iterative index n=k), stress transition model $p(S_{k+1}|S_k)$ and detection model $p(\rho_k|S_k)$ are defined. At step 1002, deviation $\rho_k$ is observed in during temporal window k, following the subject's engaging a stress-inducing task (i.e., stressor k). At step 1003, inference model $p(S_k|\rho_{1:k})$ and prior probability $p(S_0)$, which are determined experimentally.

At steps 1004 and 1005, stress-tracking algorithm 1000 computes $p(S_k|\rho_{1:k+1})$ iteratively for window k using $p(S_k|\rho\rho_{1:k})$—i.e., estimating the stress state based on the observations up to step k. Step 1004 (labeled "Step 1" in FIG. 10) is the predictive step in which the stress state in step k+1 is predicted using observations up to step k. Using Bayes' rule, the stress state $p(S_{k+1}|\rho_{1:k})$ is given by:

$$p(S_k | \rho_{1:k}) = \sum_{S_k} p(S_k | \rho_{1:k}) p(S_{k+1} | S_k) \quad (5)$$

Step 1005 (labeled "Step 2" in FIG. 10) is the correction step. At step 1005, the observations at step k+1 are used to update the prior probability, $p(S_k|\rho_{1:k})$. In other words, the stress state in the k+1-st step is computed using the observation in the k+1-st time step. Using the Chapman-Kolmogorov equation, the stress state in the k+1-st step is given by:

$$p(S_{k+1} | \rho_{1:k+1}) = \frac{p(\rho_{k+1} | S_{k+1}) p(S_{k+1} | \rho_{1:k})}{p(\rho_{k+1} | \rho_k)}. \quad (6)$$

Equation (6) may be re-written as:

$$p(S_{k+1} \mid \rho_{1:k+1}) = \frac{p(\rho_{k+1} \mid S_{k+1})p(S_{k+1} \mid \rho_{1:k})}{\sum_{S_{k+1}} p(\rho_{k+1} \mid S_{k+1})p(S_{k+1} \mid \rho_{1:k})}. \qquad (7)$$

A second experiment validates the TBN-based stress tracking algorithm of the present invention. In this experiment, as in the previous experiment, each participant is required to respond to stressors. The stressors in the second experiment may be broadly classified as Psychological, Arithmetic, and Gaming stressors:

(a). Psychological Stressor—Each user was asked to watch a series of movie clips on a home-theater system. The movie clips were chosen from a pool of honor, comedy, thriller, and drama movies. Each participant performed this task for 10 minutes after which he/she was allowed a break of 2 minutes. Participants were asked to view short scenes from movies such as "Texas Chain Saw Massacre", "The Grudge", and "Final Destination." The experimenters were in the room recording skin temperatures. A total of 10 measurements were done for every 2 minutes per participant. The task constituted a 'psychological' or an 'emotional' stressor.

(b) Arithmetic Stressor—The Arithmetic Stressor was substantially the same as the Math Stressor in the previous experiment, except that a fourth segment is included in which the participant was asked to announce each result while a looping animation is being played. The animation clip was of a ball bouncing on the ground, and the speed of bouncing increased with time. The participant was asked to announce his result during the time the ball was airborne. The Arithmetic Stressor was a mental (i.e., arithmetic) and visual stressor. 18 male and 14 female employees of DOCOMO USA Labs participated in the first three segments, during which each participant underwent a series of temperature measurements (on the index finger, thumb, palm, and forehead) just before, during, and after completing the task. 20 temperature readings were obtained for each segment. 20 participants participated in the fourth segment of the Arithmetic Stressor. The results were used to generate training data and to generate a representative conditional probability table.

(c) Gaming Stressor—Recent studies in the literature indicate that the neuroendocrine response to competition depends more on subjective factors related to the cognitive evaluation of the situation than on the outcome itself. The findings suggest that, when a participant of a competition assesses the competitive situation, the participant's body activates a psychobiological coping response. See, e.g., the article, "Coping with competitive situations in humans," A. Salvador, Neuroscience & Biobehavioral Reviews, Vol. 29, No. 1, pp. 195-205, February~2005.

Based on these findings, the participants of the experiment were asked to engage in a combination of multiplayer combat and racing games, including the popular video games "Halo 3," "Assassins' Creed," and "Need for Speed." "Halo" and "Assassins' Creed" are action-adventure video games in which the player assumed the role of a fictional character and followed a plot. While "Halo" is a first-person combat game, "Assassins' Creed" is a third-person fighting game. Both games can engage the player intensely with their game plots, characters, and graphics. In each game, the participant strived to maintain his/her game character alive. On the other hand, "Need for Speed" was a racing game. All the games were chosen to simulate scenarios of 'staying alive' or 'winning a race' (i.e., scenarios in which the fight-flight system of the participants are activated), which increase stress levels. Initially, 20 participants were each allowed 5 minutes of practice, playing against the computer. In order to facilitate ease of temperature measurements, the participants were asked to remain seated. The gaming consoles used were PS2 console operated by each participant using both hands, and a PS2 USB PC gun, which may be operated by the participant using one hand. A series of temperature measurements (on the index finger, thumb, palm, and forehead) were made on each participant just before and after the participant played the game. In order to obtain enough training data, each participant played with at least 3 other players including the computer. However, the actual data used in the experiment are collected from a round-robin competition involving all the participants, with each game lasting for 5-10 minutes. In total, 10 skin temperature readings were taken every 2 minutes.

Previous works such as Liao Articles I and II and the Rigas Article considered conditional probability tables (CPTs) generated from, for example, the disclosures of the Ortony Article, the Picard Book, the Rosekind Article, the Sherry Article or the Zhang Article. In one embodiment, a learning algorithm (e.g., the expectation maximization (EM) algorithm) fixes and refines the missing parameters and trains the DBN. Using data obtained empirically, the present invention provides 'qualitative' CPTs, such as Table 1 and Table 2. As discussed above, the present invention infers stress from the statistical deviations in temperature measurements in the temporal windows. In the present invention, there is a need for generating a new conditional probability for the detection model, $p(\rho_k \mid S_k)$, which is the probability that temperature deviation $\rho_k$ at step k is realized by the stress state $S_k$ at step k. Similarly, another conditional probability that is generated is the probability that a task is stressful, i.e., p(stress|task). For this experiment, 20 participants (14 male and 6 female employees of DOCOMO USA Labs) provide the conditional probability tables (the "training data").

The different tasks were designed to engage the participants differently. As discussed above, variations in skin temperature deviation $\rho_k$ are specific to a task. Based on the training data, 4 ranges of $\rho_k$ (shown in Table 1) can be mapped to 4 discernable stress levels, labeled respectively, 'Null,' 'Low,' 'Moderate,' and 'High.' For simplicity's sake, only 4 stress levels were chosen. The next step was to relate a specific task and the stress inferred by observing $\rho_k$, and the conditional probabilities are shown in Table 2. The participants were also asked to provide a number (between 0 and 1) to indicate how stressful he/she considered the task was. Every time a response was asked, the participant was presented with simple 2-digit arithmetic tasks, and the response times were recorded before and after or during a stress stimulus. The data corroborated the "ground truth," and allowed the conditional probabilities to be generated. For example, it was seen that about 75-80% of the participants found the gaming stressors to be highly stressful. Almost 60-70% of the participants found the different segments of arithmetic stressor to be moderately to highly stressful.

TABLE 1

Conditional probabilities for stress and temperature deviations, i.e., for computing the probability, $p(\rho_k | stress)$.

| Stress Levels | Temperature Deviations $\rho_k$ (in Fahrenheit) | | | |
| --- | --- | --- | --- | --- |
| | $\rho_k < 0.5$ | $0.5 < \rho_k < 1.5$ | $1.5 < \rho_k < 2.5$ | $2.5 < \rho_k$ |
| Null | 0.9 | 0.1 | 0 | 0 |
| Low | 0.2 | 0.7 | 0.1 | 0 |
| Moderate | 0 | 0.3 | 0.6 | 0.1 |
| High | 0 | 0.1 | 0.1 | 0.8 |

TABLE 2

Conditional probabilities for stress specific to a task, i.e., for computing the probability, p (stress | task ).

| Task | Stress Levels | | | |
| --- | --- | --- | --- | --- |
| | Null | Low | Moderate | High |
| Game (Halo) | 0 | 0.1 | 0.1 | 0.80 |
| Game (Need for Speed) | 0 | 0.05 | 0.2 | 0.75 |
| Arithmetic Segment #1 | 0.1 | 0.1 | 0.7 | 0.1 |
| Arithmetic Segment #2 | 0.1 | 0.15 | 0.65 | 0.1 |
| Arithmetic Segment #3 | 0.05 | 0.1 | 0.45 | 0.4 |
| Arithmetic Segment #4 | 0.05 | 0.05 | 0.3 | 0.6 |
| Watching Sequence of Scary Movie Clips | 0.0 | 0.35 | 0.35 | 0.3 |

Outside of the training data, 3 participants (3 male employees of DOCOMO Labs) performed the tasks in a predetermined sequence continuously for 80 minutes. Each participant underwent a series of temperature measurements (on the index finger, thumb, palm, and forehead) just before, during, and upon completion of the task. A two-minute break was allowed each participant between the psychological and arithmetic stressors. The sequence of tasks was the same for all the participants. 35 minutes of the measurements from each of the 3 participants were used as practice data, while the remaining measurements were used to validate the probabilistic model.

In this second experiment, stress is again divided into three basic levels, "Low," "Moderate," and "High" stress levels. From the data of the 3 participants used to validate the probabilistic model, the 'p-value', which is the probability of the null hypothesis of observing a result independent of the stress levels associated with the tasks, was computed to be 0.0234 for the ANOVA test, and 0.004 for the Kruskal-Wallis test. Since the p-value is less than 0.05, the result is believed statistically significant, which means that stress level is found to be sensitive to the task. The low p-value establishes that the Kruskal-Wallis test result agrees with the ANOVA result. A correlation analysis was carried out which computed over time correlation coefficients between each individual measurement and a stress level. The results reveal how a measurement varies as the subject undergoes changes in stress. The coefficients show that temperature deviations are closely correlated to the stress level of the task.

Figure 11:
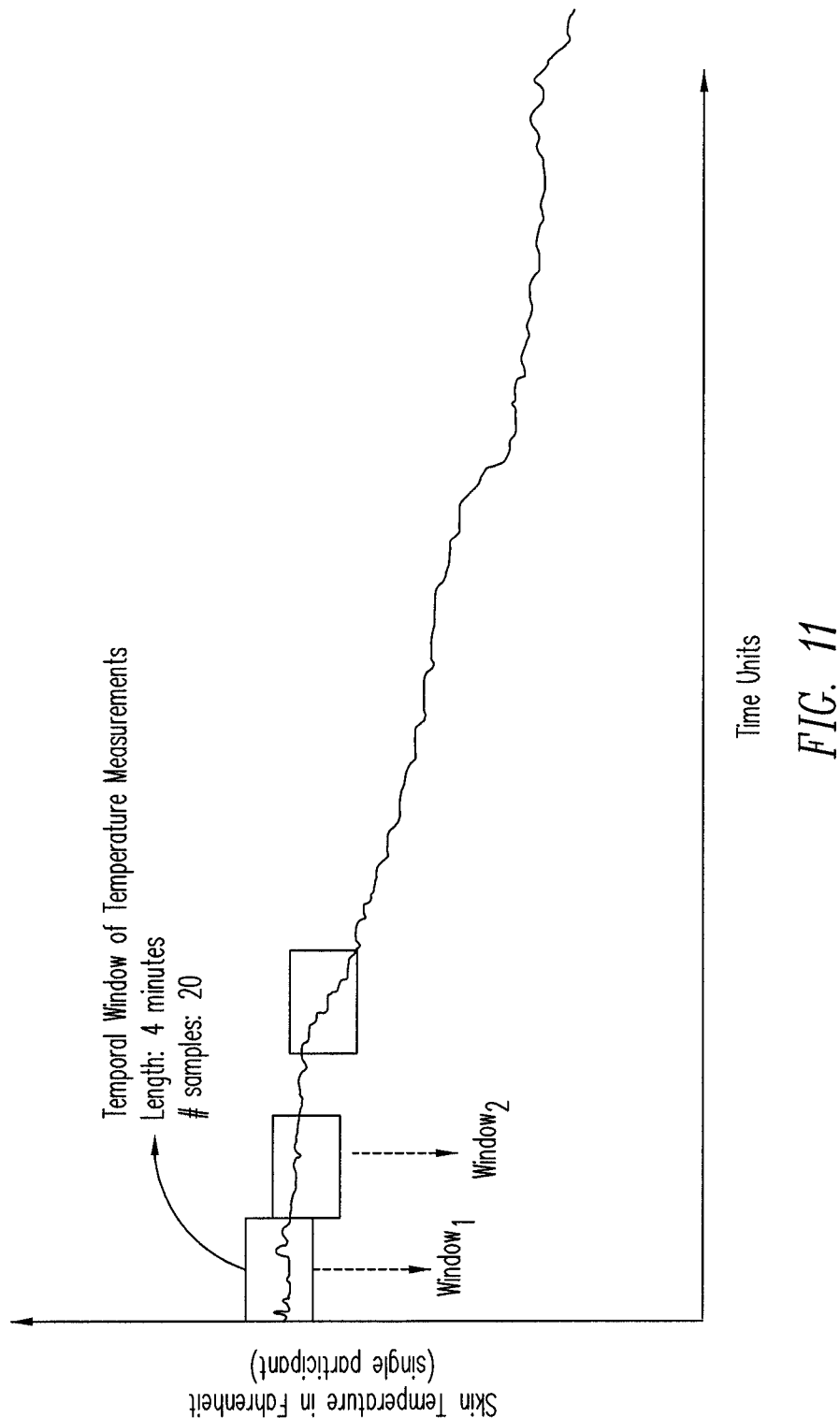
FIG. 11 plots skin temperature in one participant versus time, in which time is divided into temporal windows of 4-minute duration each, during which 20 skin temperature measurements were made.
Figure 12:
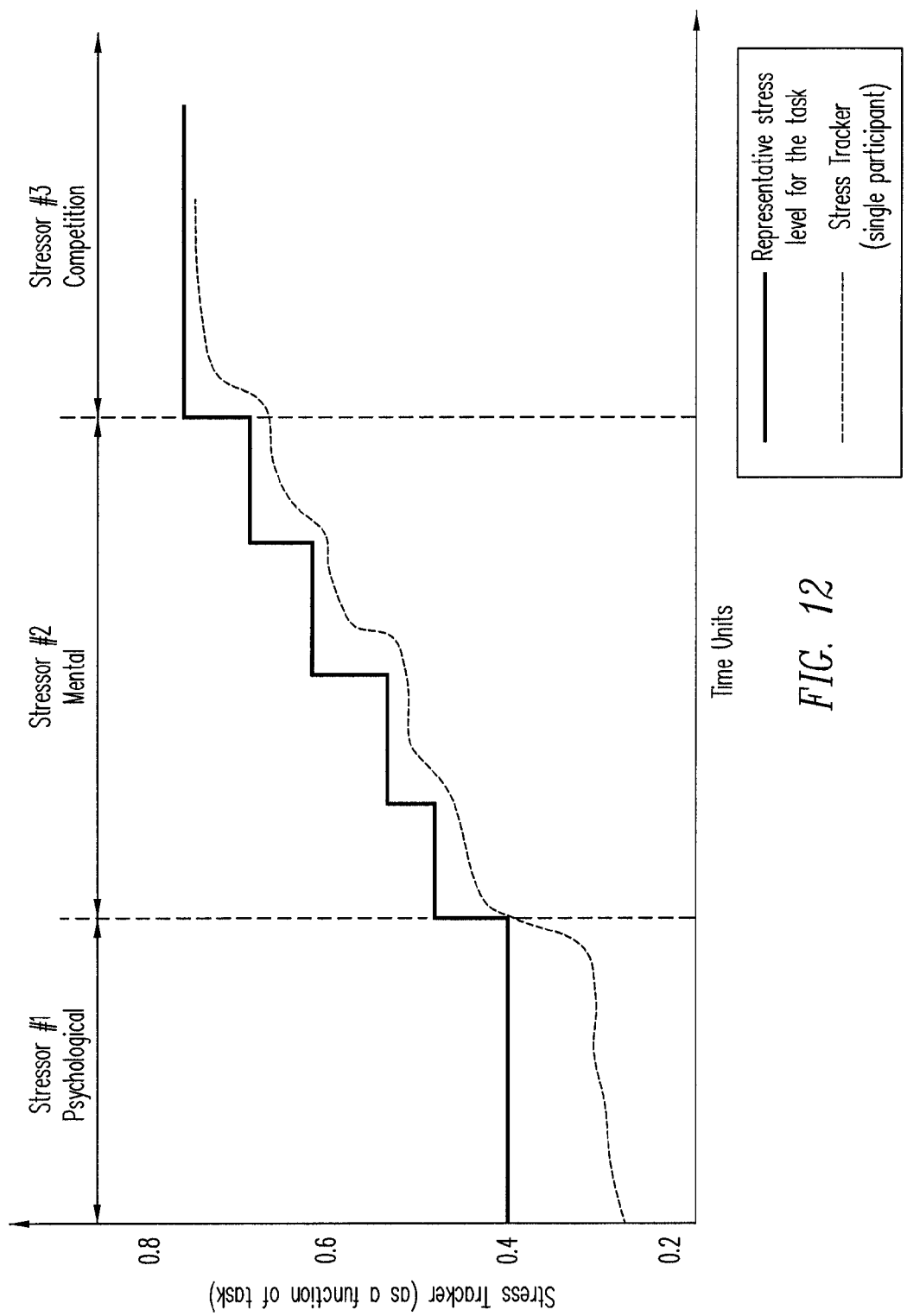
FIG. 12 plots the results of applying a Bayesian stress recognition algorithm for tracking stress transitions on a single participant, in accordance with one embodiment of the present invention; the solid line indicates expected stress levels of the activities.

FIG. 11 plots skin temperature in one participant, for temporal windows of 4-minute duration each, during which 20 skin temperature measurements were made. FIG. 12 illustrates applying Bayesian stress recognition algorithm to track stress transitions in a single participant, in accordance with one embodiment of the present invention. FIG. 11 shows that the participant's skin temperature decreased as the task became more stressful. The decrease in skin temperature was therefore an observable effect of an increased level of engagement in a task or the workload, In FIG. 12, the solid curve denotes the workload. The same workload was presented to each of the three participants. The workload was computed using Table 1, and is represented as stress levels normalized to a value between 0 and 1. In other words, the workload, as normalized, may be viewed as conditional probabilities that a certain task is stressful, based on the "training data" described above. Further, the stress level associated with a task is believed time-invariant. In FIG. 12, the dotted curve plots the values of the conditional probabilities calculated using the Chapman-Komolgorov equation, using the formulation of equation (7), for a single participant. The quantitative conditional probabilities were used to iteratively compute the stress states for the participant. As shown in FIG. 12, this probability-based approach tracks the workload (and the stress associated with the task) well for the participant, as expected from other approaches, such as those used in Liao Articles I and II. Accordingly, the results validated accurate tracking of stress levels associated with a series of tasks using measured deviations in clusters or over specified windows.

A method under the present invention may be configured to allow flexibility for a user. For example, when implemented on a wireless handheld device (e.g., a cellular telephone), the user may assign a 'size' for the sampling window. Second, as deviations in temperature measurements are observed over a temporal window, the probability of instantaneous spikes and false alarms are reduced. Finally, task-induced temperature fluctuations can be more closely tracked if the number of samples in a window is increased or the duration of the window is shortened.

Figure 13:
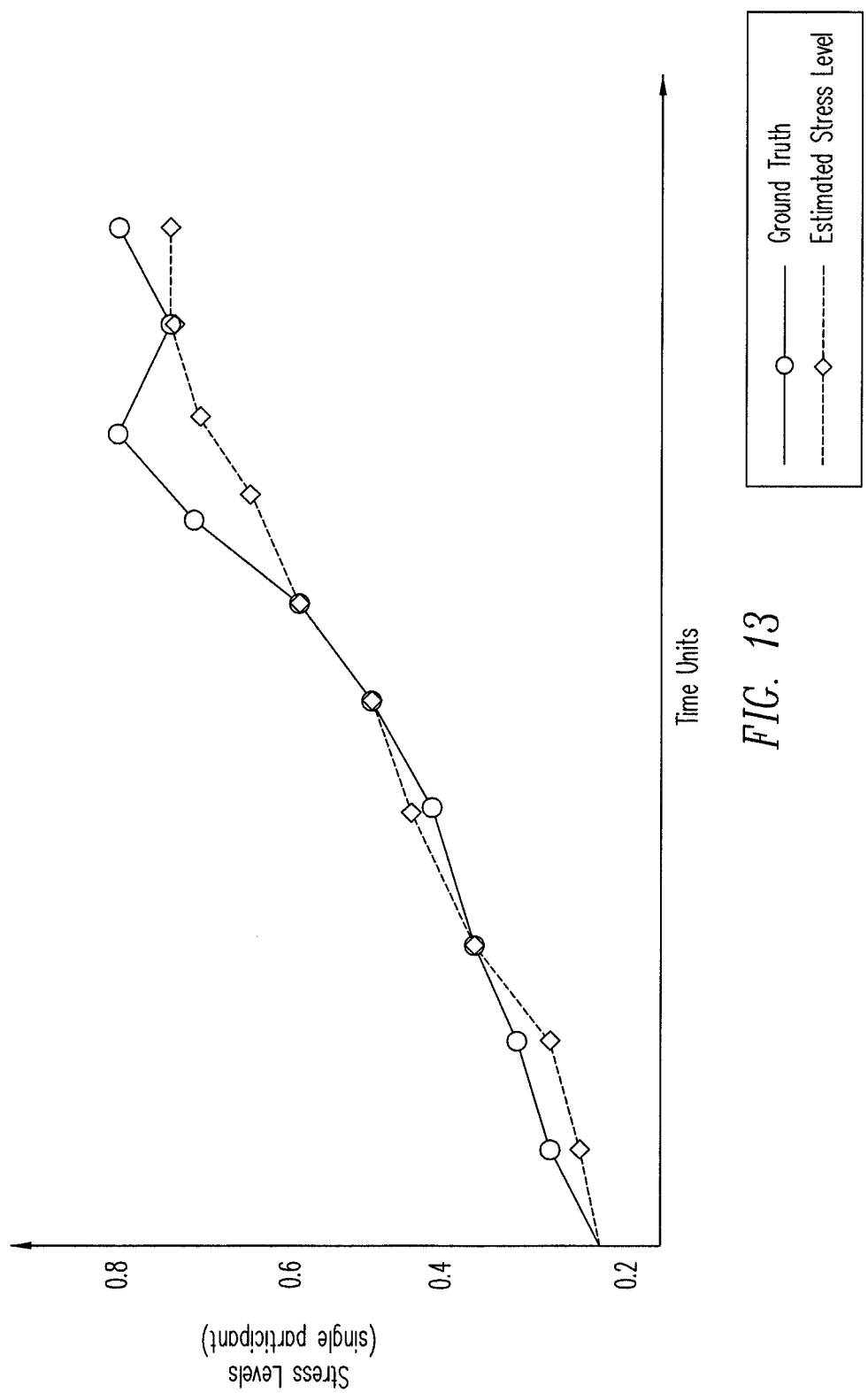
FIG. 13 plots an estimated stress level relative to an "actual stress level" derived from measured biometric data.

FIG. 13 plots an estimated stress level relative to "actual, stress level." The "actual stress level" is computed using the "training data" described above, selecting from the responses from the participants of the experiment as to their rating on a scale of 0.0 to 1.0 of the stress level associated with each task. As mentioned above, at every instance a response was collected, the participant also performed some simple tasks and the response times were used to validate the "ground truth." Even though the ground-truth is believed sometimes unreliable, the participants' responses validated the TBN-based stress recognition algorithm.

The above detailed description is provided to illustrate specific embodiments of the present invention and is not intended to be limiting. Numerous variations and modifications within the scope of the present invention are possible. The present invention is set forth in the following claims.

We claim:

1. A method for detecting a subject's stress level associated with an activity, comprising:
   connecting the subject to a sensor that senses a value of a biometric;
   during the activity,
   repeatedly sensing the value of the biometric over each of a plurality of time windows;
   computing, for each time window, a difference between each sensed biometric value in the time window and an ambient value to determine a maximum difference for the time window and a minimum difference for the time window;
   computing, for each time window, a deviation, for the sensed biometric values in the time window by subtracting the time window's minimum difference from the time window's maximum difference; and detecting the stress level based on the computed deviations for the time windows, wherein detecting the stress level further comprises inferring a stress state transition from time window to time window based on a temporal Bayesian Network (TBN) model and corresponding computed deviations.

2. A method as in claim 1, wherein the value of the biometric is a skin temperature measurement.

3. A method as in claim 1, wherein the TBN model is updated at a given time step by
(a) predicting a stress state for the given time step based on a conditional probability of a hidden stress state of an immediate previous time step given observable values of one or more previous time steps, including the immediate previous time step; and
(b) computing the hidden stress state of the given time step using the predicted stress state of the given time step and the observable values of the given time step.

4. A method as in claim 3, wherein the TBN model includes a state transition model, an inference model and a detection model.

5. A method as in claim 4, wherein the state transition model is based on a conditional probability of the hidden stress state at the given time step, given the hidden stress state of the immediate previous time step.

6. A method as in claim 4, wherein the inference model is based on a conditional probability of the hidden stress state of the immediate previous time step, given the observable values of one or more previous time steps, including the observable values of the immediate previous time step.

7. A method as in claim 1, wherein missing parameters of the TBN model is provided by a procedure based on an expectation maximization algorithm.

8. A method as in claim 1, wherein the method is implemented in a wireless handheld device.

\* \* \* \* \*